United States Patent
Fuimaono et al.

(12)

(10) Patent No.: US 6,245,054 B1
(45) Date of Patent: Jun. 12, 2001

(54) GUIDING SHEATH EXCHANGE SYSTEM

(76) Inventors: Kristine B. Fuimaono, 19685 E. Golden Bough Dr., Covina, CA (US) 91724; Mimi L. Pham, 280 E. Del Mar Blvd., #117, Pasadena, CA (US) 91101; Wilko van Erp, Oldenoert 166, 9351 KS Leek (NL); James C. Perry, 13867 Lake Poway Rd., Poway, CA (US) 92064

( * ) Notice: Subject to any disclaimer, the term of this patent is extended or adjusted under 35 U.S.C. 154(b) by 0 days.

(21) Appl. No.: 09/417,684

(22) Filed: Oct. 14, 1999

Related U.S. Application Data

(60) Provisional application No. 60/107,729, filed on Nov. 9, 1998.

(51) Int. Cl.$^7$ ................................................ A61M 25/00
(52) U.S. Cl. ............................................ 604/523; 600/585
(58) Field of Search .................................. 600/585, 433, 600/434; 604/523, 526, 528, 529

(56) References Cited

U.S. PATENT DOCUMENTS

| | | | |
|---|---|---|---|
| 4,935,017 | * | 6/1990 | Sylvanowicz ......................... 604/523 |
| 4,991,602 | * | 2/1991 | Amplatz et al. ...................... 600/585 |
| 5,354,297 | * | 10/1994 | Avitall .................................. 606/45 |
| 5,363,847 | * | 11/1994 | Viera .................................... 600/585 |
| 5,448,993 | * | 9/1995 | Lynch et al. .......................... 600/585 |
| 5,507,300 | * | 4/1996 | Mukai et al. ......................... 600/585 |
| 5,680,873 | * | 10/1997 | Berg et al. ............................ 600/585 |
| 6,001,068 | * | 12/1999 | Uchino et al. ........................ 600/585 |

OTHER PUBLICATIONS

J.D. Kugler et al., "Ablation of Left–Sided Accessory Pathways: Transatrial, Retrograde, or Coronary Sinus Approach?", "Nonpharmacological Therapy of Arrhythmias for the 21$^{st}$ Century", Futura Publishing Company, Inc., 1998; pp. 73–87.

A. S. Manolis, MD, et al., "Radiofrequency ablation of left–sided accessory pathways: Transaortic versus transseptal approach ", American Heart Journal, Nov. 1994, pp. 896–900.

J.H. O'Keefe et al., "The Transseptal Approach for Left Heart Catheterization", "Interventional Cardiology", 1989, Chapter 8; pp. 107–119.

*Primary Examiner*—Cary O'Connor
*Assistant Examiner*—Pamela Wingood
(74) *Attorney, Agent, or Firm*—Christie, Parker & Hale, LLP

(57) ABSTRACT

A guiding sheath exchange system comprises first and second guiding sheaths and an exchange dilator. Each guiding sheath has a lumen extending therethrough. The first guiding sheath has a first predefined curve at its distal end and the second guiding sheath has a second predefined curve at its distal end different from the first predefined curve. The exchange dilator comprises a flexible tubing having a generally constant diameter along its length, two tapered ends and a lumen therethrough. The guiding sheath exchange system is used for replacing the first guiding sheath having a distal end that is in the patient's heart with the second guiding sheath. The replacement method comprises inserting the distal end of the exchange dilator into the proximal end of the lumen of the first guiding sheath and feeding the distal end of the exchange dilator through the lumen so that it extends distal the distal end of the first guiding sheath. The first guiding sheath is removed from the patient's body while the distal end of the exchange dilator is left in the body. The proximal end of the exchange dilator is inserted into the distal end of the lumen of the second guiding sheath. The distal end of the second guiding sheath is fed into the body over the exchange dilator so that the distal end of the second guiding sheath is in the heart.

32 Claims, 6 Drawing Sheets

OTHER PUBLICATIONS

J. Philip Saul, MD, et al., "Catheter Ablation of Accessory Atrioventricular Pathways in Young Patients: Use of Long Vascular Sheaths, the Transseptal Approach and a Retrograde Left Posterior Parallel Approach", American College of Cardiology, Mar. 1993, JACC vol. 21, No. 3, pp. 571–583.

R. De Ponti et al., "Trans–septal catheterization for radiofrequency catheter ablation of cardiac arrhythmias: Results and safety of a simplified method", The European Society of Cardiology, 1998, 19, pp. 943–950.

* cited by examiner

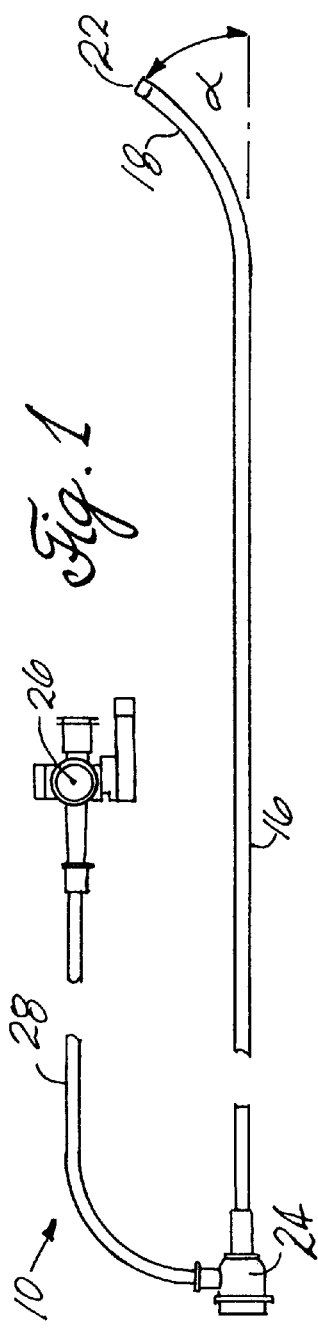
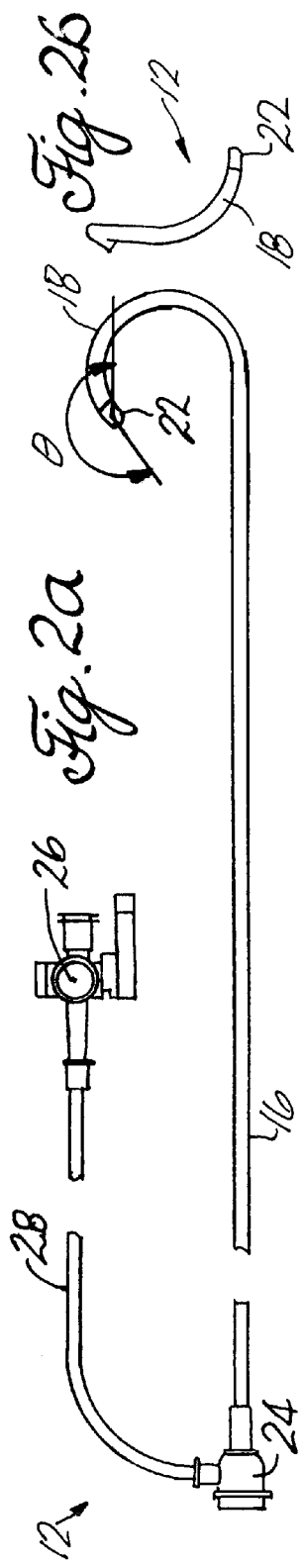
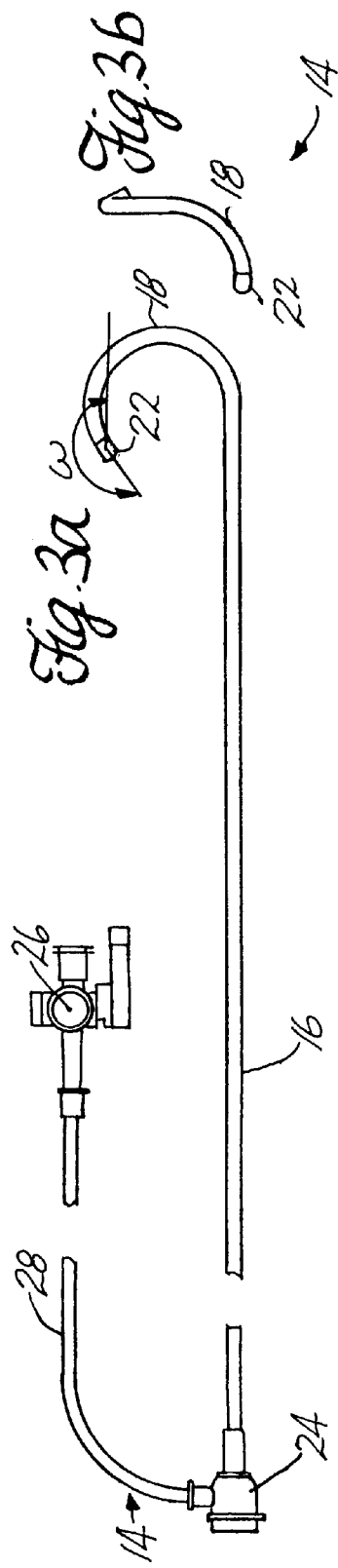

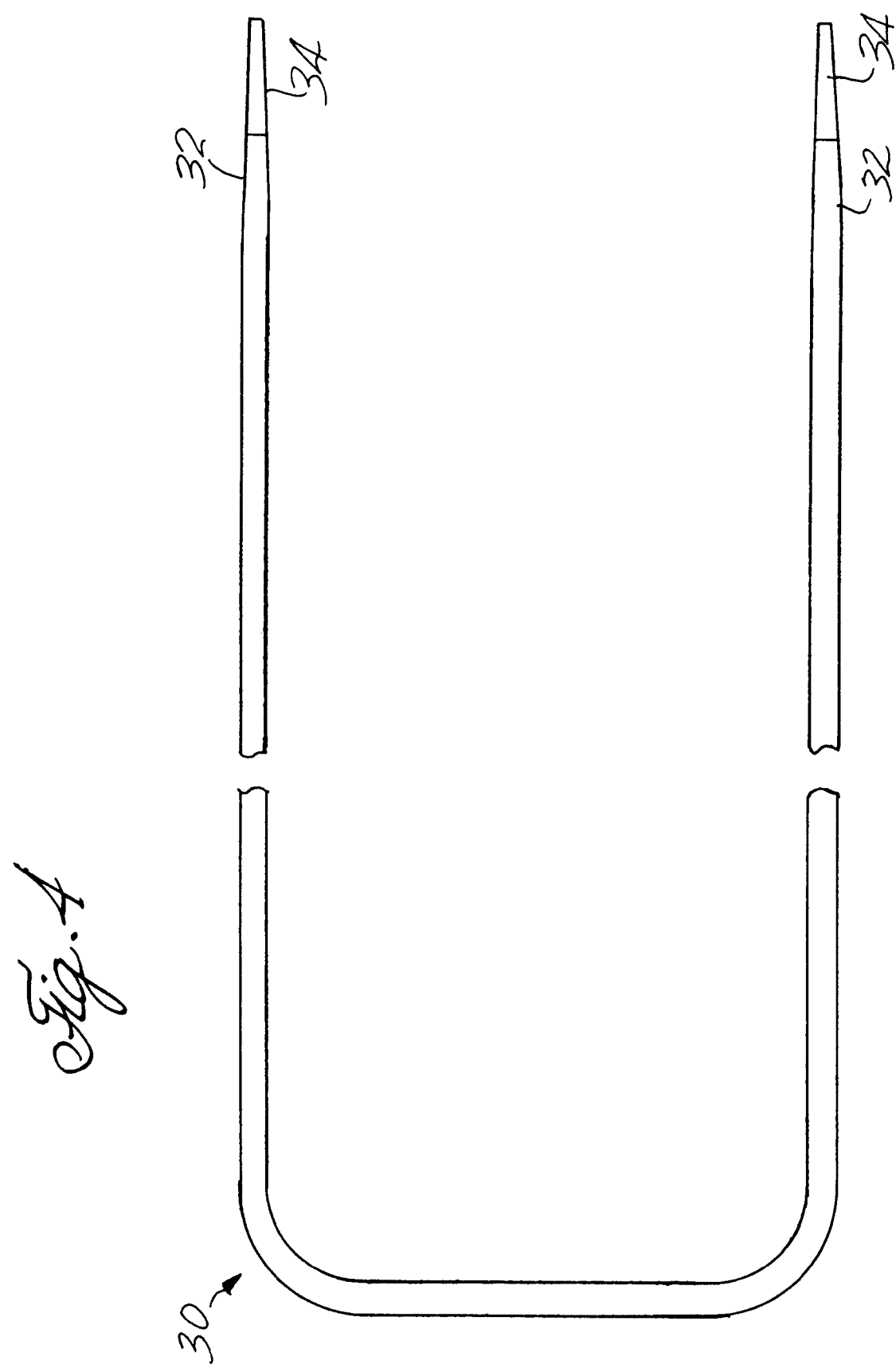

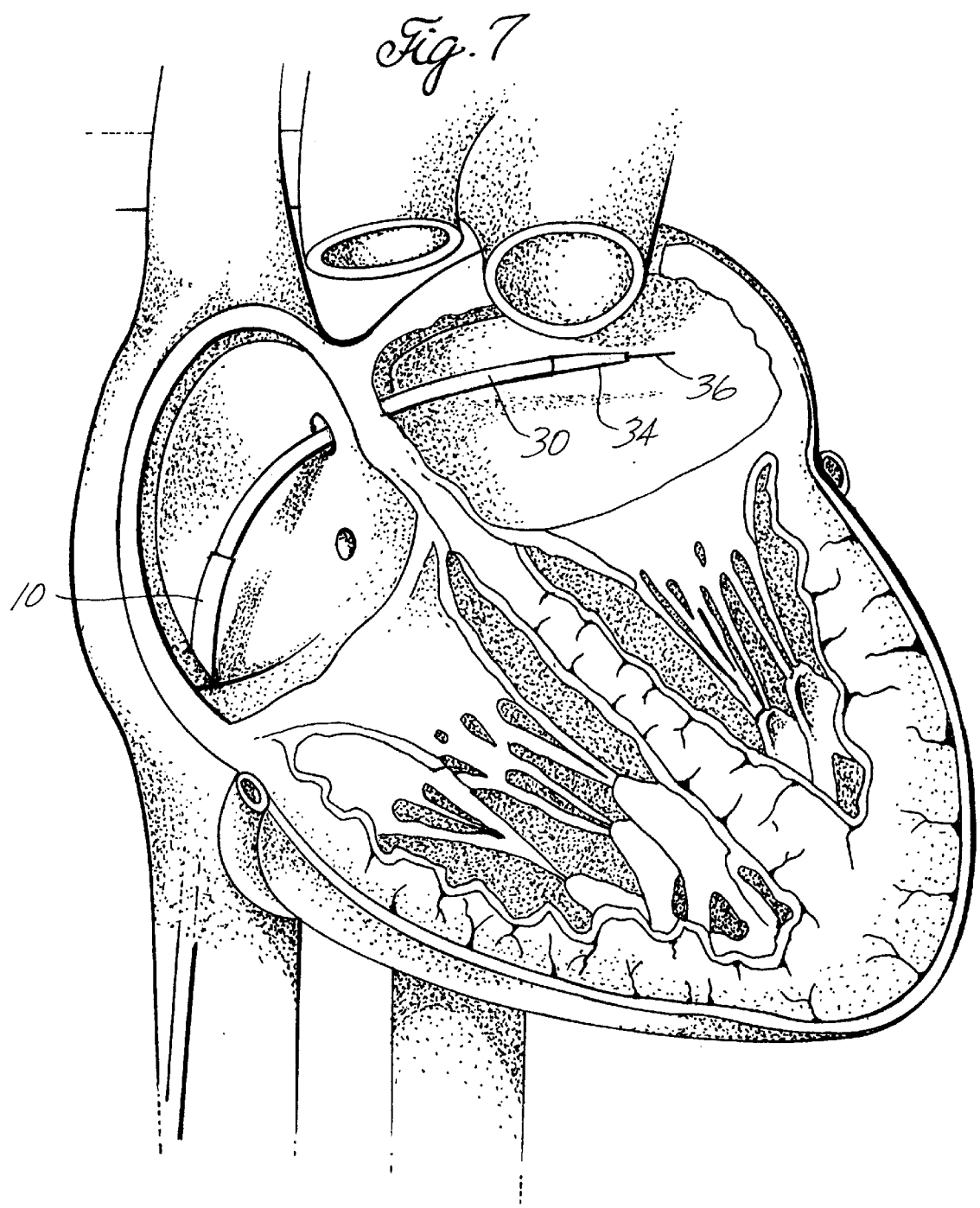

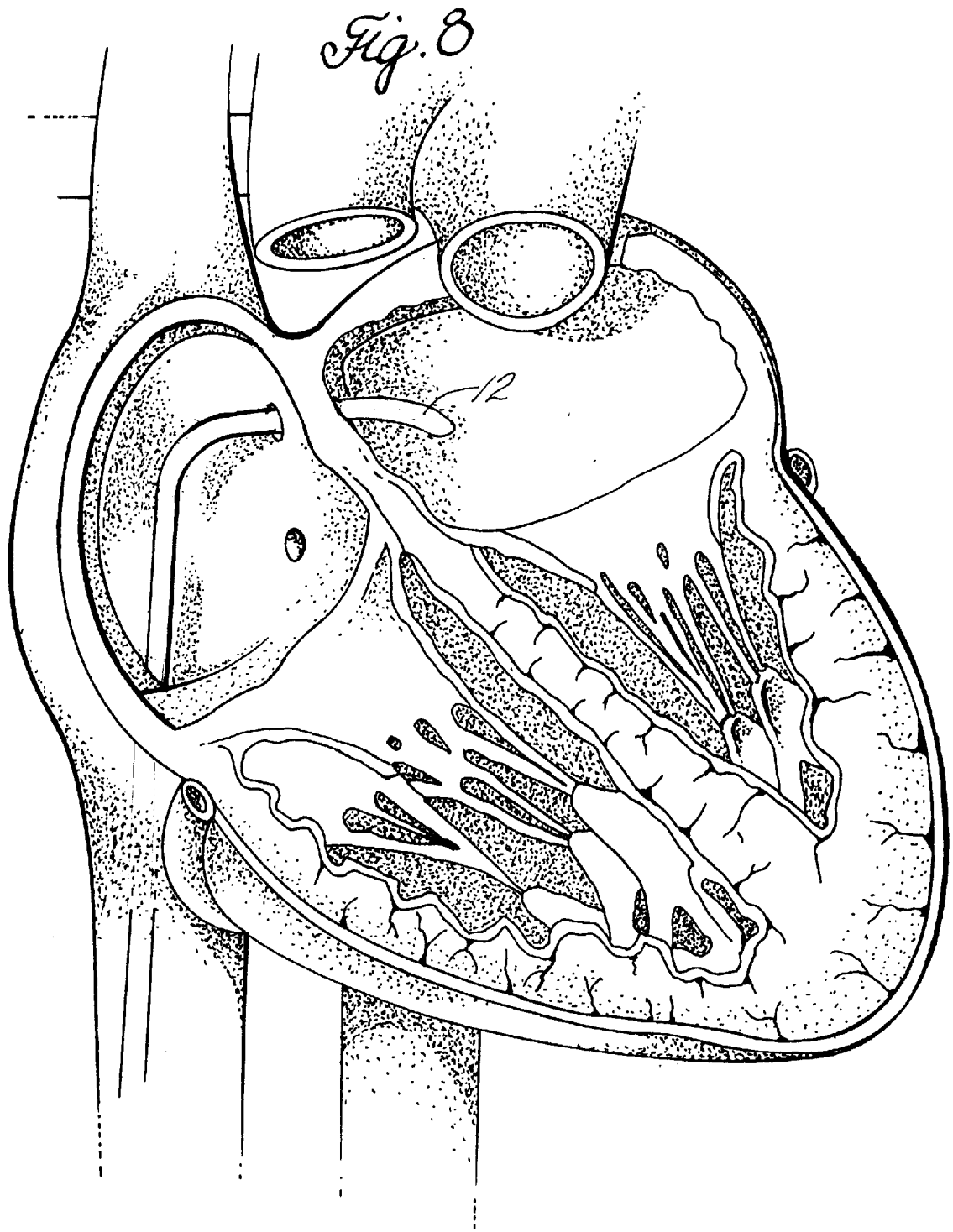

GUIDING SHEATH EXCHANGE SYSTEM

CROSS-REFERENCE TO RELATED APPLICATION

This application claims the benefit of U.S. Provisional patent application No. 60/107,729, filed Nov. 9, 1998, the entire disclosure of which is incorporated herein by reference.

BACKGROUND OF THE INVENTION

Historically, left heart catheterization has been most commonly performed by the retrograde aortic approach. The transseptal approach, which involves needle perforation of the atrial septum, was less often used due to risk of perforating the right or left atrial free walls or aorta. The traditional transseptal approach is described in De Ponti, et al., "Trans-septal catheterization for radiofrequency catheter ablation of cardiac arrhythmias", European Heart Journal (1998), Vol. 19, pages 943–50, the disclosure of which is incorporated herein by reference.

In recent years, however, use of transseptal technique has gained more widespread use with the introduction of technical modifications and products in the interventional area that have improved the safety and ease of performing the procedure, and the desire to ablate left-sided arrhythmiogenic substrates. Guiding sheaths are of particular benefit to physicians in performing left-sided ablation procedures as the sheaths provide stable means of delivering and supporting the deflectable ablation catheter on the left side. When a guiding sheath is used, direct access to the mitral annulus and the anterior and posterior walls can be attained. In addition, the long procedure times associated with the treatment of more complex arrhythmias, such as atrial fibrillation, necessitate the use of guiding sheaths to provide stability and directional control of the ablation catheter.

In some cases, a tachycardia substrate ablation site may be in a location that is difficult to reach with the curve on a standard guiding sheath and/or ablation catheter. A sheath with a more acute curve may be desirable. Performing a transseptal procedure initially with such a curve may be inadvisable, however, due to the tendency for such a sheath to redirect the transseptal needle away from the desired septal puncture site and increase the risk of the procedure. However, removal of the standard guiding sheath for replacement with a different curved sheath can result in loss of left atrial transseptal position. This could require a repeat transseptal puncture, which presents a challenge in a heparinized patient. Accordingly, a need exists for an improved transseptal left heart catheterization method.

SUMMARY OF THE INVENTION

The present invention provides a unique system and method particularly useful for performing left heart catheterization using the transseptal approach.

In one embodiment, the invention is directed to an exchange dilator for use with a guiding sheath for introduction into the heart. The exchange dilator comprises a flexible tubing having a generally constant diameter along its length, two tapered ends and a lumen therethrough. The exchange dilator permits a physician to replace a first guiding sheath having a given curve with a second guiding sheath having a different desired curve while the distal end of the dilator is maintained within the heart. Accordingly, the physician can maintain the left atrial transseptal position when exchanging the guiding sheaths.

In another embodiment, the invention is directed to a guiding sheath exchange system comprising an exchange dilator as described above and a guidewire capable of fitting within the lumen of the exchange dilator and having a length greater than the length of the exchange dilator. When the system is used in connection with a guiding sheath that has a valve at its proximal end for hemostatis, the system preferably further comprises a guidewire funnel. The guidewire funnel comprises a generally tubular body having a tapered distal end and a lumen therethrough. The guidewire funnel is inserted into the proximal end of the guiding sheath into the valve to facilitate introduction of the guidewire into the distal end of the valve. The funnel has a length ranging from about 1 inch to about 5 inches.

In yet another embodiment, the invention is directed to a guiding sheath exchange system comprising first and second guiding sheaths and an exchange dilator as described above. Each guiding sheath has proximal and distal ends and at least one lumen extending therethrough. The first guiding sheath has a first predefined curve at its distal end and the second guiding sheath has a second predefined curve at its distal end different from the first predefined curve. The dual-tapered exchange dilator facilitates replacement of the first guiding sheath with the second guiding sheath.

In still another embodiment, the invention is directed to a method for replacing a first guiding sheath with a second guiding sheath. In accordance with the method, the distal end of an exchange dilator, as described above, is inserted into the proximal end of the lumen of the first guiding sheath. The distal end of the exchange dilator is fed through the lumen so that it extends distal the distal end of the first guiding sheath. The first guiding sheath is removed from the patient's body while the distal end of the exchange dilator is left in the body. The proximal end of the exchange dilator is inserted into the distal end of the lumen of the second guiding sheath. The distal end of the second guiding sheath is introduced into the body over the dilator so that the distal end of the second guiding sheath is in the heart.

In even another embodiment, the invention is directed to a method for replacing a first guiding sheath with a second guiding sheath. The method comprises introducing the distal end of an exchange dilator, as described above, and the distal end of a guidewire into the proximal end of the lumen of the first guiding sheath. The distal end of the exchange dilator and the distal end of the guiding sheath are fed through the lumen so that they extend distal the distal end of the first guiding sheath. The first guiding sheath is removed from the patient's body while the exchange dilator and guidewire are left in the body. The proximal end of the guidewire is introduced into the distal end of the lumen of the second guiding sheath. The second guiding sheath is introduced over the exchange dilator so that the distal end of the second guiding sheath is in the heart. In a particularly preferred embodiment of this method, the second guiding sheath has a valve near its proximal end. The method further comprises providing a guidewire funnel, as described above, and inserting the tapered distal end of the guidewire funnel into the proximal end of the second guiding sheath so that the distal end passes through the valve. The proximal end of the guidewire is introduced into the distal end of the lumen of the second guiding sheath and into the distal end of the lumen of the guidewire funnel.

In another embodiment, the invention is directed to a method for performing transseptal left heart catheterization in a patient's heart. A first guiding sheath is provided having proximal and distal ends and a lumen therethrough, and a first dilator is provided having proximal and distal ends and a lumen therethrough. The first dilator is assembled into the lumen of the first guiding sheath so that the distal end of the dilator protrudes beyond the distal end of the first guiding sheath. A first guidewire having proximal and distal ends is introduced into the patient's body so that the distal end of the guidewire is in the right atrium of the patient's heart. The assembled guiding sheath and dilator are passed over the first guidewire into the right atrium. A needle having proximal and distal ends is introduced into the lumen of the dilator and advanced therethrough until the distal end of the needle is in the right atrium. The needle is pushed through the septum to create a hole in the septum. The distal end of the first guiding sheath is advanced through the hole and into the left atrium. The needle, dilator and guidewire are withdrawn from the patient's body. An exchange dilator, as described above, is provided. A second guidewire is introduced into the lumen of the exchange dilator. The distal ends of the second guidewire and exchange dilator are advanced into the proximal end of the first guiding sheath until the exchange dilator and second guidewire enter the left atrium. The first guiding sheath is removed from the patient's body while the exchange dilator and second guidewire are maintained in the left atrium. The proximal end of a second guidewire is inserted into the distal end of the lumen of the second guiding sheath. The second guiding sheath is advanced over the exchange dilator so that the distal end of the second guiding sheath is in the left atrium. The second guidewire and exchange dilator are removed from the patient's body. An electrophysiology catheter is introduced into the lumen of the second guiding sheath so that the distal end of the catheter is positioned beyond the distal end of the second guiding sheath, and the electrophysiology catheter is used to ablate tissue within the left atrium.

DESCRIPTION OF THE DRAWINGS

These and other features of the advantages of the present invention will be better understood by reference to the following detailed description when considered in conjunction with the accompanying drawings wherein:

FIG. 1 is a side view of a guiding sheath according to the invention having a multipurpose curve.

FIGS. 2A and 2B are side and end views, respectively, of a guiding sheath according to the invention having a posterior curve.

FIGS. 3A and 3B are side and end views, respectively, of a guiding sheath according to the invention having an anterior curve.

FIG. 4 is a side view of an exchange dilator in accordance with the invention.

FIGS. 6 to 8 are cross-sectional views of a heart showing how the exchange dilator and guiding sheaths are used together in accordance with the invention.

DETAILED DESCRIPTION OF THE INVENTION

Figure 5:
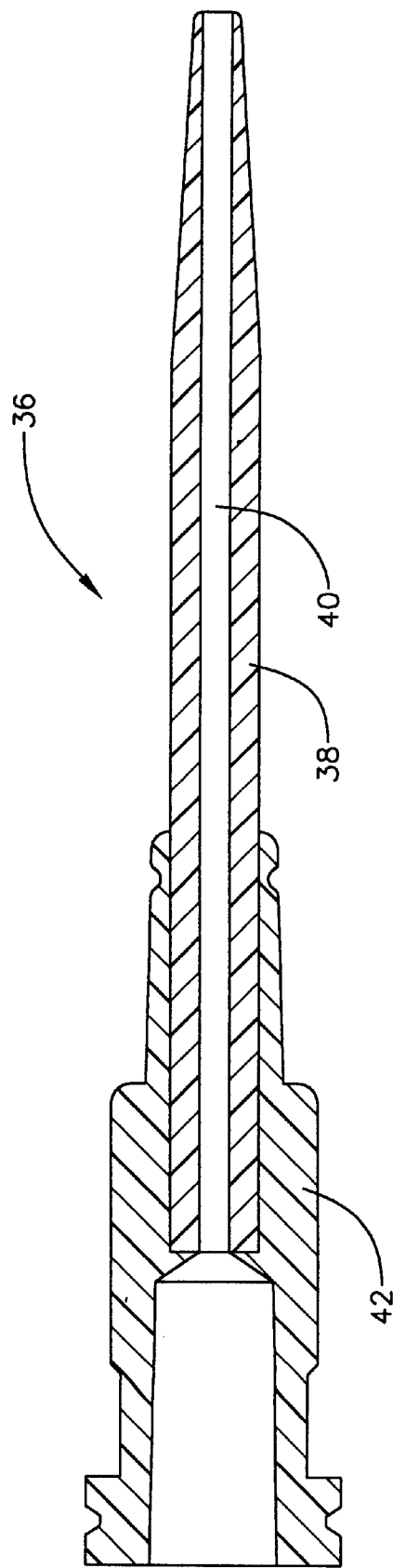
FIG. 5 is a side cross-sectional view of a guidewire funnel according to the invention.

In accordance with the invention, a guiding sheath exchange system is provided that is particularly useful in performing left heart catheterization. The system comprises at least two guiding sheaths having different curves and an exchange dilator, and preferably also comprises one or more guidewires and a standard dilator.

In a preferred embodiment, the system comprises three guiding sheaths 10, 12 and 14, each having a proximal end and a distal end. Each guiding sheath has a body 16 having a single lumen therethrough. The body 16 of each guiding sheath is generally straight with a curved distal end 18. Each sheath preferably has a different shaped curve.

As shown in FIG. 1, the first guiding sheath 10 has a multipurpose curve. With the multipurpose curve, the distal end is at an angle a relative to the axis of the body ranging from about 45° to about 110°, preferably from about 70° to about 80°, with a radius of curvature ranging from about 1.5 inches to about 2 inches, more preferably about 1.6 inches. This type of guiding sheath is particularly useful for transseptal punctures.

The second guiding sheath 12, depicted in FIG. 2, has a posterior curve. The third guiding sheath 14, depicted in FIG. 4, has an anterior curve. Examples of sheaths having such curves are described in U.S. patent application No. 09/112,463, filed Jul. 9, 1998, entitled "Guiding Sheath Having Three-Dimensional Distal End", the entire disclosure of which is incorporated by reference.

The guiding sheaths 10, 12 and 14 can be of any suitable construction known in the art. In a preferred embodiment, each guiding sheath has a useable length ranging from about 55 cm to about 80 cm, more preferably about 62 cm. As used herein, the term "useable length" refers to the length of the guiding sheath, dilator, guidewire or other devise that can be put into the body. Preferably each sheath has an outer diameter ranging from 0.125 inch to about 0.140 inch, more preferably about 0.132 inch, and an inner diameter ranging from about 0.105 inch to about 0.115 inch, more preferably about 0.110 inch (8 French). Preferably the sheaths are designed so that they can be used with catheters having an outer diameter up to about 8 French. In a particularly preferred embodiment, each sheath comprises an inner layer made of Teflon™ for increased lubricity, an outer layer made of nylon, and stainless steel wire braiding therebetween for improved torque, support and kink resistance. Preferably each sheath comprises a plurality of different durometers of material along its length to vary the stiffness of the sheath along its length. A higher durometer material is used nearer the proximal end and along the majority of the length of the sheath to yield a stiffer segment, which provides the added support required to manipulate the guiding sheath during cannulation. Increasingly softer durometer materials are used toward the distal end of each sheath to provide a flexible atraumatic distal end. This flexibility minimizes restriction of the ablation catheter's tip deflection during deployment. Additionally, this design allows the physician to anatomically shape the sheath, which custom fits itself to the natural patient anatomy during a procedure.

A preferred method for manufacturing a guiding sheath as described above involves first positioning extruded Teflon™ tubing over a mandrel. The Teflon™ tubing is overlaid with stainless steel wire braiding. An extruded nylon body and tip segments are slid over the stainless steel braiding. The nylon body and tip segments are fused to the Teflon™ layer. The mandrel is then removed from the sheath.

The distal end of each sheath is provided a radiopaque tip 22 to provide high visibility for precise intracardiac placement. Preferably the radiopaque tip comprises a low durometer polyurethane with radiopaque filler, such as that sold under the name BRITE TIP® by Cordis Corporation (Miami Lakes, Fla.). This material is also atraumatic for vessel protection during cannulation.

The proximal end of each sheath is provided with a valve 24, preferably made of nylon, for hemostatis. A particularly preferred valve for use in connection with the present invention is a hexacuspid cut valve such as the disclosed in U.S. Pat. No. 4,798,594, the entire disclosure of which is incorporated herein by reference. The valve 24 is connected to a suitable stopcock 26 by tubing 28 made of any suitable plastic, preferably polyurethane. A suitable stopcock and tubing arrangement for use with the present invention is described in U.S. patent application No. 09/112,463.

As mentioned above, the system of the invention also includes an exchange dilator 30, as shown in FIG. 4, which has a lumen therethrough for insertion of a guidewire. The exchange dilator 30 has two ends 32, each of which is tapered, unlike a traditional dilator, which has only one tapered end. The dual-taper design permits transseptal exchange of guiding sheaths without loss of intracardiac position, as described in more detail below. Preferably both ends 32 of the exchange dilator 30 are the same.

The exchange dilator 30 can be of any suitable construction. A preferred design comprises a body made of polyethylene with barium sulfate. Preferably a coating is provided over the body for lubricity within a guiding sheath. A suitable coating comprises silicone, such as MDX4-4159, a mixture of aminofunctional polydimethylsiloxane copolymer in mixed aliphatic and isopropanol solvents (commercially available from Dow Corning™, Midland, Mich.). The length of the body (i.e., not including the tapered ends 32) has an outer diameter ranging from about 0.075 inch to about 0.150 inch, preferably from about 0.103 inch to about 0.109 inch, more preferably about 0.106 inch. The body, including the tapered ends, has an inner diameter sufficient to receive a guidewire, preferably from about 0.020 inch to about 0.050 inch, more preferably from about 0.040 inch to about 0.045 inch, still more preferably about 0.042 inch. Preferably the exchange dilator 30 has a length greater than the length of the guiding sheaths with which it is used to facilitate removal of the guiding sheaths from the exchange dilator while maintaining intracardiac position, as described in more detail below. Preferably the exchange dilator 30 has a length ranging from about 115 cm to about 155 cm, more preferably from about 125 cm to about 145 cm, still more preferably from about 135 cm to about 140 cm. In a preferred embodiment, the exchange dilator 30 is at least twice as long as the guiding sheath(s) with which it is used.

At the ends 32 of the dilator are provided radiopaque tips 34 to enhance the visibility of the tips during intracardiac placement. In a preferred design, each radiopaque tip 34 is made from polyethylene with tungsten and has a length ranging from about 5 mm to about 10 mm, preferably about 7 mm.

If desired, the system can further include a standard dilator, i.e., having a standard length and only one tapered end, for initial introduction of a guiding sheath. A preferred standard dilator has a construction similar to the exchange dilator 30, described above, with only one radiopaque tip and a length slightly longer than the guiding sheath(s) with which it is used, preferably from about 60 cm to about 80 cm, more preferably about 67 cm.

The system can also include one or more suitable guidewires, as is known in the art. In a particularly preferred embodiment, two guidewires are provided, a first guidewire for use with the standard dilator and a second guidewire for use with the exchange dilator. Preferably the guidewires are made of stainless steel and have an outer diameter ranging from about 0.030 inch to about 0.038 inch, preferably about 0.032 inch. Each guidewire preferably has a useable length about twice as long as the dilator with which it is used. The first guidewire has a length preferably ranging from about 130 cm to about 160 cm, more preferably about 150 cm. The second guidewire has a length preferably ranging from about 250 cm to about 280 cm, more preferably about 260 cm.

Another component that is preferably provided in the inventive system is a guidewire funnel. As shown in FIG. 5, the guidewire funnel 38 comprises a tubular body 38 having proximal and distal ends and a lumen 40 therethrough. A holding piece 42 is mounted at the proximal end of the body. The distal end of the tubular body is tapered. The funnel preferably has a length ranging from about 1 inch to about 5 inches, more preferably from about 1.5 inches to about 2 inches. In use, the distal end of the guidewire funnel is inserted into the proximal end of the valve of a guiding sheath. The tapered distal end of the guidewire funnel pushes the valve open to facilitate insertion of a guidewire through the distal end of the valve. Without the use of a guidewire funnel, it is difficult to insert the guidewire through the distal side of the valve because the valve has a relatively small opening.

Figure 6:
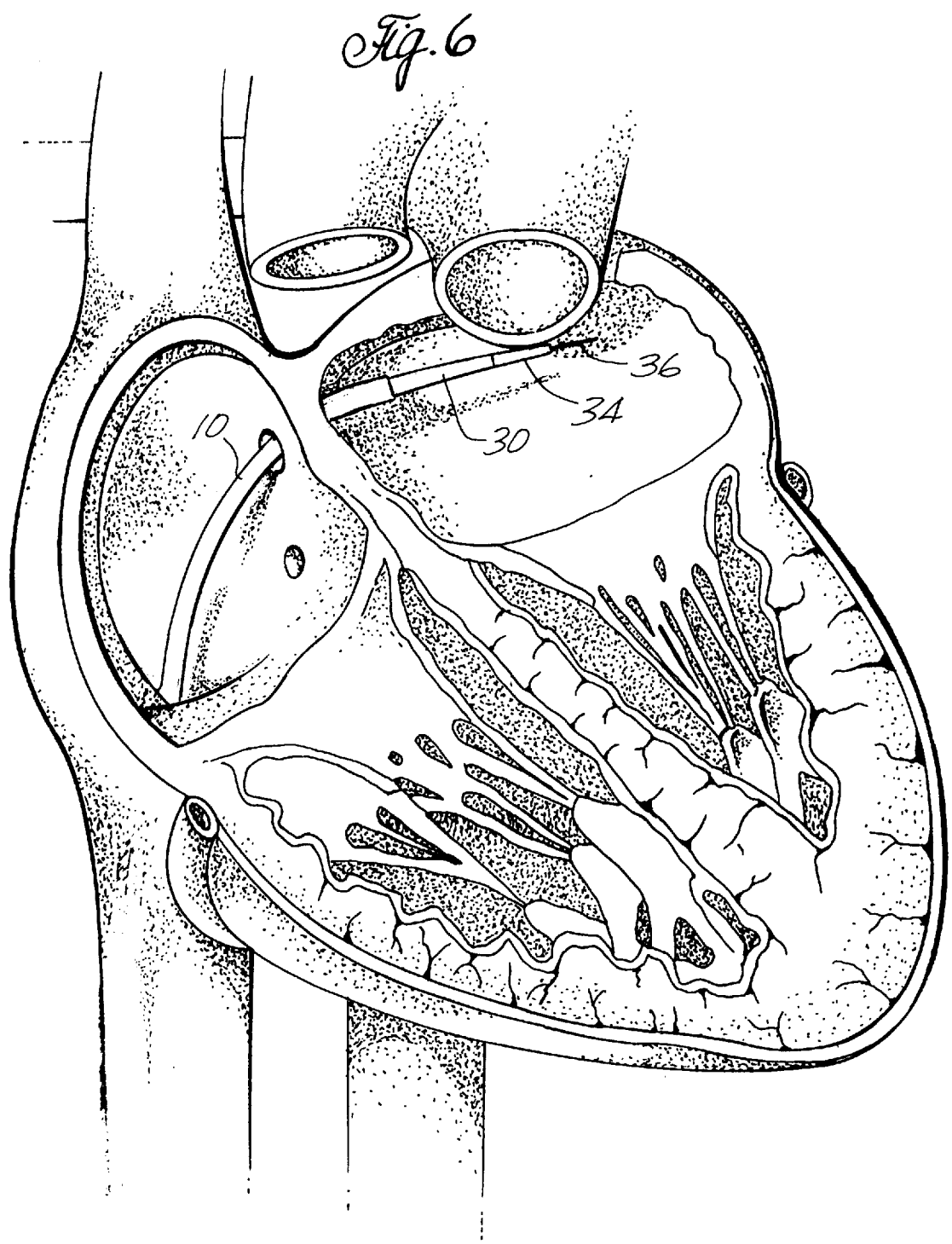

In another embodiment, the invention is directed to a method for replacing an existing guiding sheath in the heart with a second sheath during a catheterization procedure so that the second guiding sheath is placed in substantially the same position as the existing sheath was located. In accordance with this method, and as shown in FIG. 6, an exchange dilator 30, as described above, is provided along with a long guidewire 36, such as the second guidewire described above. The long guidewire is inserted into the lumen of the exchange dilator. The exchange dilator and guidewire are introduced into the existing sheath 10.

Preferably the guidewire and exchange dilator are secured in a relatively distant, stable location during removal of the existing guiding sheath to minimize trauma and prevent inadvertent induction of arrhythmias. For example, for a left atrial exchange, the guidewire is preferably positioned in a left pulmonary vein. For right atrial exchanges, the guidewire is preferably positioned in the superior vena cava. For retrograde left ventricular approaches, the guidewire is positioned in the left ventricular apex, and for right ventricular exchanges, in the pulmonary artery. The exchange dilator is positioned beyond the distal end of the existing sheath in a stable location, such as in a proximal pulmonary vein orifice. The existing sheath 10 is withdrawn, as shown in FIG. 7, with the guidewire 36 and exchange dilator 30 left in position.

The proximal end of the guidewire is introduced into the second guiding sheath, preferably into the distal end of the second guiding sheath so that the guidewire is fed backwards toward the valve. The second guiding sheath is then introduced over the exchange dilator to the optimal intracardiac location. The second guiding sheath is held in place while the guidewire and exchange dilator are withdrawn. The second guiding sheath 12 is allowed to safely assume its contoured shape, as shown in FIG. 8, and is positioned in the same location that the existing sheath was originally positioned.

In a particularly preferred embodiment the invention is directed to a method for performing transseptal left heart catheterization, e.g., for treating a left heart tachycardia. The method includes a transseptal procedure and a sheath exchange procedure.

For the transseptal procedure, a first guiding sheath, preferably a guiding sheath having a multipurpose curve, is assembled with a standard dilator, i.e., with the dilator contained within the lumen of the guiding sheath. The dilator should protrude beyond the distal end of the guiding sheath a sufficient amount so that the entire tapered end is exposed to ensure a smooth transition. A suitable needle, such as a Brockenbrough™ transseptal needle (commercially available from USCI-C.R. Bard, Tewksbury, Mass.) or a BRK™ transseptal needle (commercially available from St. Jude Medical/Daig, St. Paul, Minn.), is passed through the lumen of the dilator, and the length of the needle that protrudes beyond the distal end of the dilator is noted. The needle is then removed from the system.

As is known in the art, an introducer is inserted into the groin. A first guidewire (e.g., preferably having a length ranging from about 130 cm to about 160 cm, more preferably about 150 cm) is inserted into the introducer up the superior vena cava (SVC) beyond the insertion of or into the innominate vein toward the patient's left. The introducer is removed, holding groin pressure and maintaining position of the wire.

The assembled sheath and dilator is passed over the first guidewire to the high SVC/innominate vein position. The tip of the dilator is positioned in the high SVC or in the innominate vein, and the first guidewire is removed. The system is aspirated and flushed.

A needle is introduced into the lumen of the dilator and advanced therethrough until the needle tip is seen, fluoroscopically, to be about 3 to 5 cm from the distal end of the dilator. The radiopaque tip of the dilator appears dark and allows easy fluoroscopic location. The needle is positioned about 1 to 2 mm proximal to the radiopaque tip. The system preferably points medially on the anteroposterior projection and directly toward or slightly posterior on the lateral projection. The entire system is held by the physician with the left hand holding the sheath at the groin entry site and the right hand holding the needle, sheath and dilator as a single unite. The entire system is then withdrawn, inferiorly toward the right atrium and slowly as a unit. The site for the transseptal puncture is the central atrial septum, just below the limbus, which tends to be the thinnest area of the septum. When in proper position, the system is held steady, and the needle is advanced to its fullest extend, keeping the distal end of the dilator at the septum. The needle is pushed through the septum for transseptal puncture.

When the needle is in the left atrium, the entire system is advanced to allow the dilator to slide through the septum and enter the left atrium as well. The entire system, with the needle and dilator in the left atrium, is advanced slightly, and the guiding sheath is slid over the dilator and needle into the left atrium. Alternatively, the dilator and guiding sheath can be advanced together over the needle into the left atrium.

Once the distal end of the guiding sheath is well into the left atrium, the needle is withdrawn several centimeters into the dilator. The needle can tear the guiding sheath if it is not inside the dilator during subsequent removal. The dilator and needle are together withdrawn while the physician maintains the distal end of the guiding sheath at its exact location in the left atrium. The guiding sheath is aspirated and flushed and connected to record left atrial pressure.

A suitable electrophysiology (EP) catheter is passed through the guiding sheath to the left atrium. Examples of suitable EP catheters for use in connection with the inventive methods include, for example, a CELSIUS™ ablation catheter (commercially available from Biosense Webster, Inc., Diamond Bar, Calif.). The distal end of the catheter preferably does not extend beyond the distal end of the guiding sheath to avoid perforation. A strong downward deflection is then placed on the EP catheter, and the guiding sheath is withdrawn slightly, revealing left-sided electrograms from the EP catheter.

If the tachycardia substrate mapping or ablation site is in a location difficult to reach or maintain with standard catheter capabilities, the physician may find a curved long sheath desirable, in which case the doctor performs a sheath exchange procedure. With the sheath exchange procedure, the original guiding sheath (i.e., with the multipurpose curve) is initially maintained in the left atrium. The EP catheter is withdrawn, allowing blood to fill the lumen of the guiding sheath, which is then aspirated and flushed.

A second guidewire (i.e., having a preferred length of from about 250 cm to about 280 cm, more preferably about 260 cm) is inserted into the lumen of an exchange dilator (i.e., a dilator having two tapered ends and a preferred length of from about 115 cm to about 155 cm, as described above). Preferably the second guidewire extends from the distal end of the exchange dilator a length of about 3 to 5 cm. The second guidewire and dilator are introduced into the proximal end of the first guiding sheath until the guidewire enters the left atrium. Preferably the guidewire is then advanced and manipulated to enter the left upper pulmonary vein and secured in the distal lung. The distal end of the exchange dilator is then advanced distally into the pulmonary vein, with the guidewire maintained beyond the distal end of the dilator to prevent the dilator from acting as a needle or blade. The first guiding sheath is removed over the exchange dilator and guidewire, with the exchange dilator and guidewire maintained in position. Because the proximal end of the exchange dilator is tapered, the first guiding sheath can be easily slid off. Additionally, the increased length of the exchange dilator and second guidewire (discussed above) allows complete control of the dilator and guidewire so that the physician does not lose the dilator and/or guidewire within the body of the guiding sheath during removal of the guiding sheath.

A second guiding sheath having the desired curve is prepared by inserting the proximal end of the second guidewire into the distal end of the lumen of the sheath. A guidewire funnel is inserted into the proximal end of the second guiding sheath to facilitate the retrograde passage of the second guidewire and exchange dilator out the proximal end of the sheath. With the distal end of the second guidewire and exchange dilator maintained within the pulmonary vein, the second guiding sheath is advanced by sliding it over the guidewire and dilator. Once the second guiding sheath is in place within the left atrium, the second guidewire and exchange dilator are removed from the guiding sheath, and the guiding sheath is aspirated and flushed. By this method, a stable position with the second guiding sheath having the desired curve is achieved without losing position, without damaging cardiac structure and while maintaining the puncture hole.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An exchange dilator for use with a guiding sheath for introduction into the heart, the exchange dilator comprising a flexible tubing having a generally constant diameter along its length, a tapered proximal end, a tapered distal end, and a lumen therethrough.

2. An exchange dilator according to claim 1, wherein each tapered end comprises a radiopaque material.

3. An exchange dilator according to claim 2, wherein the radiopaque material comprises tungsten.

4. An exchange dilator according to claim 1 having a length ranging from about 115 cm to about 155 cm.

5. An exchange dilator according to claim 1 having a length ranging from about 125 cm to about 145 cm.

6. An exchange dilator according to claim 1 having a length ranging from about 135 cm to about 140 cm.

7. A guiding sheath exchange system comprising:
   an exchange dilator according to claim 1;
   a guidewire capable of fitting within the lumen of the exchange dilator and having a length greater than the length of the exchange dilator.

8. A guiding sheath exchange system according to claim 7, further comprising a guidewire funnel comprising a generally tubular body having a tapered distal end and a lumen therethrough, wherein the funnel has a length ranging from about 1 inch to about 5 inches.

9. A guiding sheath exchange system according to claim 7, wherein the exchange dilator has a length ranging from about 115 cm to about 155 cm, and the guidewire has a length ranging from about 250 cm to about 280 cm.

10. A guiding sheath exchange system comprising:
    first and second guiding sheaths, each guiding sheath having proximal and distal ends and at least one lumen extending therethrough, wherein the first guiding sheath has a first predefined curve at its distal end and the second guiding sheath has a second predefined curve at its distal end different from the first predefined curve; and
    an exchange dilator according to claim 1.

11. A guiding sheath exchange system according to claim 10, wherein the exchange dilator has a length ranging from about 115 cm to about 155 cm.

12. A guiding sheath exchange system according to claim 10, wherein the exchange dilator has a length ranging from about 125 cm to about 145 cm.

13. A guiding sheath exchange system according to claim 10, wherein the exchange dilator has a length ranging from 135 cm to about 140 cm.

14. A guiding sheath exchange system according to claim 10, wherein each guiding sheath has a length ranging from about 55 cm to about 70 cm.

15. A guiding sheath exchange system according to claim 14, wherein the exchange dilator has a length ranging from about 125 cm to about 145 cm.

16. A guiding sheath exchange system according to claim 10, further comprising a guidewire.

17. A guiding sheath exchange system according to claim 16, wherein the guidewire has a length ranging from about 250 cm to about 280 cm.

18. A guiding sheath exchange system according to claim 12, further comprising a guidewire having a length ranging from about 250 cm to about 280 cm.

19. A guiding sheath exchange system according to claim 16, further comprising a guidewire funnel comprising a generally tubular body having a tapered distal end and a lumen therethrough, wherein the funnel has a length ranging from about 1 inch to about 5 inches.

20. A method for replacing a first guiding sheath having a lumen therethrough, a proximal end outside a patient's body and a distal end that is in the patient's heart with a second guiding sheath having proximal and distal ends and a lumen therethrough, the method comprising:
    providing an exchange dilator according to claim 1;
    inserting the distal end of the exchange dilator into the proximal end of the lumen of the first guiding sheath;
    feeding the distal end of the exchange dilator through the lumen so that it extends distal the distal end of the first guiding sheath;
    removing the first guiding sheath from the patient's body while leaving the distal end of the exchange dilator in the body;
    inserting the proximal end of the exchange dilator into the distal end of the lumen of the second guiding sheath; and
    introducing the distal end of the second guiding sheath into the body over the dilator so that the distal end of the second guiding sheath is in the heart.

21. A method according to claim 20, wherein the exchange dilator has length greater than twice the length of the first guiding sheath.

22. A method according to claim 20, wherein the exchange dilator has a length ranging from about 115 cm to about 155 cm and the first guiding sheath has a length ranging from about 55 cm to about 70 cm.

23. A method according to claim 22, wherein the exchange dilator has a length ranging from about 125 cm to about 145 cm.

24. A method according to claim 22, wherein the exchange dilator has a length ranging from 135 cm to about 140 cm.

25. A method for replacing a first guiding sheath having a lumen therethrough, a proximal end outside a patient's body and a distal end that is in the patient's heart with a second guiding sheath having proximal and distal ends and a lumen therethrough, the method comprising:
    providing an exchange dilator according to claim 1;
    providing a guidewire having a proximal end and a distal end;
    introducing the distal end of the exchange dilator and the distal end of the guidewire into the proximal end of the lumen of the first guiding sheath;
    feeding the distal end of the exchange dilator and the distal end of the guiding sheath through the lumen so that they extend distal the distal end of the first guiding sheath;
    removing the first guiding sheath from the patient's body while leaving the exchange dilator and guidewire in the body;
    introducing the proximal end of the guidewire into the distal end of the lumen of the second guiding sheath; and
    introducing the second guiding sheath over the exchange dilator so that the distal end of the second guiding sheath is in the heart.

26. A method according to claim 25, wherein the exchange dilator has a length greater than twice the length of the first guiding sheath.

27. A method according to claim 25, wherein the exchange dilator has a length ranging from about 115 cm to about 155 cm and the first guiding sheath has a length ranging from about 55 cm to about 70 cm.

28. A method according to claim 27, wherein the guidewire has a length ranging from about 250 cm to about 280 cm.

29. A method according to claim 25, wherein the second guiding sheath has a valve near its proximal end, and wherein the method further comprises:

provides a guidewire funnel comprising a generally tubular body having a tapered distal end and a lumen therethrough, wherein the funnel has a length ranging from about 1 inch to about 5 inches;

inserting the tapered distal end into the proximal end of the second guiding sheath so that the distal end passes through the valve;

introducing the proximal end of the guidewire into the distal end of the lumen of the second guiding sheath and into the distal end of the lumen of the guidewire funnel.

30. A method for performing transseptal left heart catheterization in a patient's heart, the method comprising:

providing a first guiding sheath having proximal and distal ends and a lumen therethrough;

providing a first dilator having proximal and distal ends and a lumen therethrough;

assembling the first dilator into the lumen of the first guiding sheath so that the distal end of the dilator protrudes beyond the distal end of the first guiding sheath;

introducing a first guidewire having proximal and distal ends into the patient's body so that the distal end of the guidewire is in the right atrium of the patient's heart;

passing the assembled guiding sheath and dilator over the first guidewire into the right atrium;

introducing a needle having proximal and distal ends into the lumen of the dilator and advancing the needle therethrough until the distal end of the needle is in the right atrium;

pushing the needle through the septum to create a hole in the septum;

advancing the distal end of the first guiding sheath through the hole and into the left atrium;

withdrawing the needle, dilator and guidewire from the patient's body;

providing an exchange dilator according to claim 1;

introducing a second guidewire having proximal and distal ends into the lumen of the exchange dilator;

advancing the distal ends of the second guidewire and exchange dilator into the proximal end of the first guiding sheath until the exchange dilator and second guidewire enter the left atrium;

removing the first guiding sheath from the patient's body while maintaining the exchange dilator and second guidewire in the left atrium;

providing a second guiding sheath having proximal and distal ends and a lumen therethrough;

inserting the proximal end of the second guidewire into the distal end of the lumen of the second guiding sheath;

advancing the second guiding sheath over the exchange dilator so that the distal end of the second guiding sheath is in the left atrium;

removing the second guidewire and exchange dilator from the patient's body;

introducing an electrophysiology catheter into the lumen of the second guiding sheath so that the distal end of the catheter is positioned beyond the distal end of the second guiding sheath; and using the electrophysiology catheter to ablate tissue within the left atrium.

31. A method according to claim 30, wherein the first guidewire is the same as the second guidewire.

32. A method according to claim 30, wherein the first dilator is the same as the exchange dilator.

* * * * *